(12) United States Patent
Vanasse et al.

(10) Patent No.: US 8,945,131 B2
(45) Date of Patent: Feb. 3, 2015

(54) CANAL SIZER AND ASSOCIATED METHOD

(75) Inventors: Thomas M. Vanasse, Thomaston, CT (US); Andrew M. Jacobs, Fort Wayne, IN (US); Gordon R. Young, Fort Wayne, IN (US); Charles W. Jaggers, Warsaw, IN (US)

(73) Assignee: DePuy Synthes Products, LLC, Raynham, MA (US)

( * ) Notice: Subject to any disclaimer, the term of this patent is extended or adjusted under 35 U.S.C. 154(b) by 1405 days.

(21) Appl. No.: 12/697,680

(22) Filed: Feb. 1, 2010

(65) Prior Publication Data

US 2010/0131022 A1    May 27, 2010

Related U.S. Application Data

(62) Division of application No. 10/717,404, filed on Nov. 19, 2003, now abandoned.

(51) Int. Cl.
*A61F 2/46* (2006.01)
*A61B 19/00* (2006.01)
(Continued)

(52) U.S. Cl.
CPC .............. *A61B 19/46* (2013.01); *A61B 5/1076* (2013.01); *A61F 2/30723* (2013.01); *A61F 2/30724* (2013.01); *A61F 2/4657* (2013.01); *A61B 5/4504* (2013.01); *A61B 17/164* (2013.01); *A61B 2017/00539* (2013.01); *A61B 2017/00544* (2013.01); *A61B 2019/446* (2013.01); *A61B 2019/461* (2013.01); *A61B 2019/462* (2013.01); *A61F 2/36* (2013.01); *A61F 2/3662* (2013.01); *A61F 2/3676* (2013.01); *A61F 2/3859* (2013.01); *A61F 2/389* (2013.01); *A61F 2/4607* (2013.01); *A61F 2/4614* (2013.01); *A61F 2002/30616* (2013.01); *A61F 2002/30617* (2013.01); *A61F 2002/30714* (2013.01); *A61F 2002/3611* (2013.01); *A61F 2002/3625* (2013.01); *A61F 2002/3631* (2013.01); *A61F 2002/365* (2013.01);
(Continued)

(58) Field of Classification Search
USPC ........... 606/62, 65, 67, 86 R, 89, 95, 91, 102, 606/916; 623/23.15
See application file for complete search history.

(56) References Cited

U.S. PATENT DOCUMENTS 3,008,203 A    11/1961    Dagenhard
3,058,225 A    10/1962    Ward
(Continued)

FOREIGN PATENT DOCUMENTS

CA    815863    6/1969
DE    2637119   7/1953
(Continued)

OTHER PUBLICATIONS

Zimmer Versys Total Hip System Brochure, Instrumentation: pp. 9-12, 97-7800-03 Rev. 1.5mm Printed in USA 1996, 1998 Zimmer, Inc.

*Primary Examiner* — Kevin T Truong
*Assistant Examiner* — Michael Araj

(57) ABSTRACT

An instrument for measuring the medullary canal of a long bone in order to determine the proper size for a stem centralizer is provided. The instrument includes an elongated central portion defining opposed first and second ends and a contact portion. The contact portion extends from the first end or the second end of the elongated central portion. The contact portion has a contact area for contact with the medullary canal and defines a relief area for providing clearance between the instrument and the medullary canal.

6 Claims, 18 Drawing Sheets

(51) Int. Cl.
  A61B 5/107 (2006.01)
  A61F 2/30 (2006.01)
  A61B 5/00 (2006.01)
  A61B 17/16 (2006.01)
  A61B 17/00 (2006.01)
  A61F 2/36 (2006.01)
  A61F 2/38 (2006.01)
  A61F 2/40 (2006.01)

(52) U.S. Cl.
  CPC . A61F 2002/4077 (2013.01); A61F 2002/4615 (2013.01); A61F 2002/4631 (2013.01); A61F 2002/4658 (2013.01); A61F 2002/4659 (2013.01); A61F 2002/4662 (2013.01); A61F 2250/0064 (2013.01); A61F 2250/0089 (2013.01); A61F 2250/0097 (2013.01)
  USPC ...................................................... 606/86 R

(56) References Cited

U.S. PATENT DOCUMENTS

| | | |
|---|---|---|
| 3,200,984 A | 8/1965 | Fueslein et al. |
| 3,358,869 A | 12/1967 | Palmer et al. |
| 3,738,355 A | 6/1973 | Salvatore |
| 3,740,779 A | 6/1973 | Rubricuis |
| 3,744,061 A | 7/1973 | Frost |
| 3,793,650 A | 2/1974 | Ling |
| 3,831,383 A | 8/1974 | Crank |
| 3,834,394 A | 9/1974 | Hunter et al. |
| 3,848,272 A | 11/1974 | Noiles |
| 3,866,248 A | 2/1975 | Kummer |
| 3,889,665 A | 6/1975 | Ling et al. |
| 3,924,274 A | 12/1975 | Heimke et al. |
| 3,938,504 A | 2/1976 | Dickinson et al. |
| 3,939,820 A | 2/1976 | Grayzel |
| 3,943,914 A | 3/1976 | Grenfell et al. |
| 3,987,499 A | 10/1976 | Scharbach et al. |
| 4,011,602 A | 3/1977 | Rybicki et al. |
| 4,012,796 A | 3/1977 | Weisman et al. |
| 4,013,071 A | 3/1977 | Rosenberg |
| 4,016,867 A | 4/1977 | King et al. |
| 4,065,817 A | 1/1978 | Branemark et al. |
| 4,123,806 A | 11/1978 | Amstutz et al. |
| 4,213,461 A | 7/1980 | Pevsner |
| 4,231,120 A | 11/1980 | Day |
| 4,245,359 A | 1/1981 | Stuhmer |
| 4,276,659 A | 7/1981 | Hardinge |
| 4,293,962 A | 10/1981 | Fuson |
| 4,302,855 A | 12/1981 | Swanson |
| 4,311,146 A | 1/1982 | Wonder |
| 4,327,734 A | 5/1982 | White |
| 4,337,773 A | 7/1982 | Raftopoulos et al. |
| 4,341,218 A | 7/1982 | Ü |
| 4,344,190 A | 8/1982 | Lee |
| 4,357,716 A | 11/1982 | Brown |
| 4,364,392 A | 12/1982 | Strother |
| 4,399,614 A | 8/1983 | Kertz |
| 4,447,915 A | 5/1984 | Weber |
| 4,462,394 A | 7/1984 | Jacobs |
| 4,488,549 A | 12/1984 | Lee |
| 4,516,885 A | 5/1985 | Calandra |
| 4,517,969 A | 5/1985 | Halcomb |
| 4,523,587 A | 6/1985 | Frey |
| 4,562,598 A | 1/1986 | Kranz |
| 4,566,466 A | 1/1986 | Ripple et al. |
| 4,625,722 A | 12/1986 | Murray |
| 4,627,434 A | 12/1986 | Murray |
| 4,686,973 A | 8/1987 | Frisch |
| 4,697,584 A | 10/1987 | Haynes |
| 4,745,914 A | 5/1988 | Frey |
| 4,753,405 A | 6/1988 | Camilleri |
| 4,878,791 A | 11/1989 | Kurihara et al. |
| 4,904,267 A | 2/1990 | Bruce et al. |
| 4,921,493 A | 5/1990 | Webb |
| 4,936,859 A | 6/1990 | Morscher et al. |
| 4,950,295 A | 8/1990 | Weigum et al. |
| 4,987,904 A | 1/1991 | Wilson |
| 4,994,085 A | 2/1991 | Sawai et al. |
| 5,047,035 A | 9/1991 | Mikhail et al. |
| 5,078,746 A | 1/1992 | Garner |
| 5,133,766 A * | 7/1992 | Halpern .................. 623/23.24 |
| 5,171,275 A | 12/1992 | Ling et al. |
| 5,192,283 A | 3/1993 | Ling et al. |
| 5,314,493 A | 5/1994 | Mikhail |
| 5,341,493 A | 8/1994 | Yanal et al. |
| 5,385,568 A | 1/1995 | Boebel et al. |
| 5,443,468 A | 8/1995 | Johnson |
| 5,470,336 A | 11/1995 | Ling et al. |
| 5,471,756 A | 12/1995 | Bolanos |
| 5,681,318 A | 10/1997 | Pennig et al. |
| 5,683,395 A | 11/1997 | Mikhail |
| 5,718,707 A | 2/1998 | Mikhail |
| 5,755,720 A | 5/1998 | Mikhail |
| 5,782,917 A * | 7/1998 | Carn ....................... 623/23.48 |
| 5,788,704 A | 8/1998 | Timperley |
| 5,800,437 A | 9/1998 | Gustilo |
| 5,951,606 A * | 9/1999 | Burke ..................... 623/23.15 |
| 6,042,554 A | 3/2000 | Rosenman et al. |
| 6,926,741 B2 | 8/2005 | Kolb |
| 2002/0128721 A1 | 9/2002 | Chan |

FOREIGN PATENT DOCUMENTS

| | | |
|---|---|---|
| DE | 2247560 | 10/1973 |
| EP | 0595956 B1 | 7/1976 |
| EP | 0006408 | 1/1980 |
| EP | 0058744 B1 | 9/1982 |
| EP | 0584489 A1 | 6/1993 |
| EP | 0555004 B1 | 8/1993 |
| EP | 0711535 B1 | 5/1996 |
| EP | 0853931 A2 | 12/1997 |
| EP | 0860143 A2 | 2/1998 |
| FR | 1046920 | 7/1953 |
| FR | 2662931 A1 | 6/1990 |
| GB | 1443470 | 7/1976 |
| GB | 2017503 A | 10/1979 |
| GB | 2253564 | 9/1992 |
| JP | 57-26128 | 6/1982 |
| WO | 9415544 | 7/1994 |
| WO | 9609011 | 3/1996 |

* cited by examiner

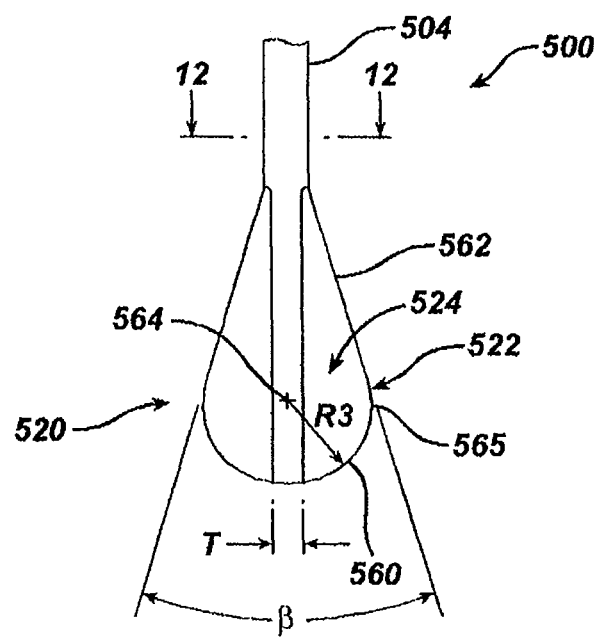
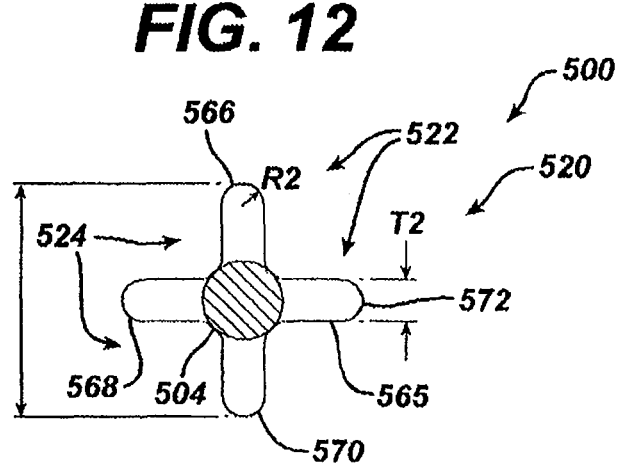

CANAL SIZER AND ASSOCIATED METHOD

CROSS-REFERENCE TO RELATED APPLICATIONS

This is a divisional patent application of U.S. patent Ser. No. 10/717,404 of the same title and filed on Nov. 19, 2003, the disclosure of which is hereby incorporated by reference.

TECHNICAL FIELD OF THE INVENTION

The present invention relates generally to the field of orthopaedics, and more particularly, to an instrument for use in arthroplasty.

BACKGROUND OF THE INVENTION

A joint within the human body forms a juncture between two or more bones or other skeletal parts. The ankle, hip, knee, shoulder, elbow and wrist are just a few examples of the multitude of joints found within the body. As should be apparent from the above list of examples of joints, many of the joints permit relative motion between the bones. For example, the motion of sliding, gliding, hinge or ball and socket movements may be had by a joint. For example, the ankle permits a hinge movement, the knee allows for a combination of gliding and hinge movements and the shoulder and hip permit movement through a ball and socket arrangement.

The joints in the body are stressed or can be damaged in a variety of ways. For example, gradual wear and tear is imposed on the joints through the continuous use of a joint over the years. The joints that permit motion have cartilage positioned between the bones providing lubrication to the motion and also absorbing some of the forces direct to the joint. Over time, the normal use of a joint may wear down the cartilage and bring the moving bones in direct contact with each other. In contrast, in normal use, a trauma to a joint, such as the delivery of a large force, from an accident, for example, an automobile accident, may cause considerable damage to the bones, the cartilage or to other connective tissue such as tendons or ligaments.

Arthropathy, a term referring to a disease of the joint, is another way in which a joint may become damaged. Perhaps the best known joint disease is arthritis, which is generally referred to a disease or inflammation of a joint that results in pain, swelling, stiffness, instability, and often deformity.

There are many different forms of arthritis, with osteoarthritis being the most common and resulting from the wear and tear of a cartilage within a joint. Another type of arthritis is osteonecrosis, which is caused by the death of a part of the bone due to loss of blood supply. Other types of arthritis are caused by trauma to the joint while others, such as rheumatoid arthritis, Lupus, and psoriatic arthritis destroy cartilage and are associated with the inflammation of the joint lining The hip joint is one of the joints that is commonly afflicted with arthropathy. The hip joint is a ball and socket joint that joins the femur or thighbone with the pelvis. The pelvis has a semispherical socket called the acetabulum for receiving a ball socket head in the femur. Both the head of the femur and the acetabulum are coated with cartilage for allowing the femur to move easily within the pelvis. Other joints commonly afflicted with arthropathy include the spine, knee, shoulder, carpals, metacarpals, and phalanges of the hand. Arthroplasty as opposed to arthropathy commonly refers to the making of artificial joint. In severe cases of arthritis or other forms of arthropathy, such as when pain is overwhelming or when a joint has a limited range of mobility, a partial or total replacement of the joint with an artificial joint may be justified. The procedure for replacing the joint varies, of course, with the particular joint in question, but in general involves replacing a terminal portion of an afflicted bone with a prosthetic implant and inserting a member to serve as a substitute for the cartilage.

The prosthetic implant is formed of a rigid material that becomes bonded with the bone and provides strength and rigidity to the joint and the cartilage substitute members chosen to provide lubrication to the joint and to absorb some of the compressive forces. Suitable materials for the implant include metals, and composite materials such as titanium, cobalt chromium, stainless steel, ceramic and suitable materials for cartilage substitutes include polyethylene. A cement may also be used to secure the prosthetic implant to the host bone.

A total hip replacement, for example, involves removing the ball shaped head of the femur and inserting a stem implant into the center of the bone which is referred to as the medullary canal or marrow of the bone. The stem implant may be cemented into the medullary canal or may have a porous coated surface for allowing the bone to heal directly to the implant. The stem implant has a neck and a ball shaped head which are intended to perform the same functions as a healthy femur's neck and a ball shaped head. The polyethylene cup is inserted into the acetabulum and has a socket for receiving the head on the stem implant.

One challenge in the proper positioning of the prosthesis during surgery is the proper position of the stem axially and rotationally. Improper positioning has been shown to limit the patient's range of motion by inducing improper leg length, inadequate lateral stem offset and non-anatomical version of the stem. Inadequate pressurization of the cement within the femoral canal has also been documented as a potential cause of improper cement technique.

Centralization of the stem within the cement mantle is also critical for success. Non-uniform or excessively thin cement mantles can induce high cement stress and subsequent cracks that may cause failure at the cement-stem-bone interfaces. The cement debris, due to abrasions, has also been shown to produce excessive third-body wear of polyethylene acetabular components as well as potentially induce osteolytic reactions and bone resorptions that may lead to stem loosening.

One device utilized to assist in the centralization of the stem is a centralizer or spacer. Centralizers or spacers are provided for fitting to the distal end of a femoral hip replacement stem in order to keep the implant stem away from the internal surface of the cavity of the bone in which this stem is to be inserted.

In the case of stems which are cemented in the bone cavity there is a space between the stem and the internal surface of the cavity of the bone in which the cement is placed. Controlling the position of the stem within the surrounding bone cement mantle is vital to long-term survivability of the replacement joint. Cement can be deposited in the bone cavity and then the stem may be inserted with the centralizer attached to the stem. Alternatively, the centralizer may be inserted into the cavity and the stem later inserted against the centralizer. It is important to try to obtain an even and intact cement mantle around the stem.

In addition to the purpose of the centralizer to properly position the stem, the centralizer may be designed to serve a second purpose, that is to separate the cement from the blood and other body fluids within the medullary canal of the bone. Such separation of cement and medullary canal fluids is exasperated by the more recent use of external pressure to assure the complete filling of the bone cavity with cement.

Known centralizers are in the form of caps which fit over the distal end of the stem and centralizers which are fixed inside of a drilled end of a stem. Centralizers are also known which are of ring form which can have a tapered inner surface corresponding to the tapered surface of the distal stem of the femoral stem on which the centralizer is located.

Centralizers or spacers in the form of a cap for insertion on the end of a hip stem with fins or wings extending outwardly from the cap which are adapted to fold circumferentially and inwardly toward the body portion of the cap.

Cemented stem systems generally utilize two components distal to the stem, a centralizer and a cement plug. The centralizers usually have fins that protrude into the cement mantle around the stem.

Due to variations in the age, gender, and size of a patient, a wide variety of distal centralizers are available for use in the medullary canal of a patient. The proper or optimum size from the available variety of sizes of the centralizer must be selected by the surgeon. When implanting a cemented stem, a surgeon has to make an educated guess using for example x-rays and templating to determine the proper sized distal centralizer to use.

Due to the two-dimensional nature of x-rays and templating, and the three-dimensional shape of the centralizer, such techniques are crude and inaccurate. Such techniques may require the removal of the first chosen centralizer and a second centralizer used or may result in a less than ideal centralizer being utilized.

Attempts have been made to provide for a more accurate way of determining the proper size for centralizer for the surgeon to use on a particular patient. For example, a canal sizer has been developed by Zimmer Holding, Inc., Warsaw, Ind.; sold as the IM Sizer, which provides for a plug having a round cross-section. This device may have a tendency to get caught in the distal canal before its proper position is reached. Also, this device is adapted for only one particular brand and style of orthopedic implant.

The present invention is adapted to overcome at least one of the aforementioned shortcomings of the prior art.

SUMMARY OF THE INVENTION

The present invention provides for a one-piece canal sizer for use in selecting a distal centralizer for use in joint arthroplasty. The one-piece sizer includes a central shaft and opposed measuring tips. According to one aspect of the present invention, the measuring tips have a shape corresponding to that of the corresponding centralizer.

According to another aspect of the present invention, a second measurement tip is connected to the sizer on the end opposed to the first measuring tip.

According to yet another aspect of the present invention, the measuring tips include spaced apart contact and relief areas to assist in the ease of inserting the canal sizer.

According to yet another aspect of the present invention, the canal sizer may include indicia in the form of, for example, spaced apart marks denoting the depth in which the canal sizer has been inserted. Such markings are useful in determining the proper size of implant stem to utilize.

According to one embodiment of the present invention, there is provided an instrument for measuring the medullary canal of a long bone in order to determine the proper size for a stem centralizer. The instrument includes an elongated central portion defining opposed first and second ends and a contact portion. The contact portion extends from the first end of the elongated central portion. The contact portion has a contact area for contact with the medullary canal and defines a relief area for providing clearance between the instrument and the medullary canal.

According to another embodiment of the present invention there is provided an instrument for measuring the medullary canal of a long bone in order to determine the proper size for a stem centralizer. The instrument includes an elongated central portion defining opposed first and second ends and a first contact portion extending from the first end of the elongated central portion. The first contact portion has a contact area for contact with the medullary canal and defines a relief area for providing clearance between the instrument and the medullary canal. The instrument also includes a second contact portion extending from the second end of the elongated central portion. The second contact portion has a contact area for contact with the medullary canal and defines a relief area for providing clearance between the instrument and the medullary canal.

According to still another embodiment of the present invention there is provided a kit for use in performing total hip arthroplasty. The kit includes a plurality of instruments. Each of the plurality of instruments is adapted for measuring the medullary canal of a long bone. Each of the plurality of instrument includes an elongated central portion defining opposed first and second ends and a contact portion. The contact portion extends from the first end of the elongated central portion. The contact portion has a contact area for contact with the medullary canal and defines a relief area for providing clearance between the instrument and the medullary canal. The kit also includes a hip stem for implantation into the medullary canal and a plurality of stem centralizers. The centralizers are for cooperation with the hip stem and for implantation into the medullary canal. Each of the plurality of stem centralizers corresponds to one of the contact portions of said plurality of instruments.

According to a further embodiment of the present invention, there is provided a method for providing joint arthroplasty. The method includes the steps of resecting a long bone, preparing the medullary canal of a long bone, providing a plurality of instruments for measuring the medullary canal of the long bone, each of the instruments including an elongated central portion defining opposed first and second ends, and a contact portion extending from the first end of the elongated central portion, the contact portion having a plurality of contact areas for contact with the medullary canal and defining a plurality of relief areas for providing clearance between the instrument and the medullary canal. The method also includes the steps of inserting one of the plurality of instruments into the canal, providing a plurality of centralizers for implanting into the medullary canal of the long bone, each of the plurality of centralizers corresponding to one of the plurality of instruments, determining the appropriateness of the one of the plurality of instruments, inserting the one of the plurality of centralizers corresponding to the one of the plurality of instruments into the canal, providing a stem, and implanting the stem in the medullary canal of a long bone.

According to yet another embodiment of the present invention, there is provided an instrument for measuring the medullary canal of a resected long bone in order to determine the proper size for a stem centralizer. The instrument includes an elongated central portion defining opposed first and second ends and a contact portion. The contact portion extends from the first end of the elongated central portion. The contact portion has a shape substantially similar to the shape of the stem centralizer on the surface opposed to the resected surface of the long bone.

The technical advantages of the present invention include the ability to select an optimum sized cement plug centralizer for a particular patient. For example, according to one aspect of the present invention, a kit for use in performing total hip arthroplasty is provided. The kit includes a plurality of instruments. Each of the instruments is adapted for measuring the canal of the femur. Each of the plurality of instruments includes a contact portion. The contact portion has a contact area for contact with the medullary canal. The kit also includes a hip stem and a plurality of stem centralizers. The instruments serve to replicate the stem centralizers such that the instruments are progressively inserted into the canal until the contact portion of an instrument is determined to be optimum. The stem centralizer corresponding to that contact portion is then inserted as the optimum size cement centralizer. The present invention provides for optimum sizing of the stem centralizer for a patient.

The technical advantages of the present invention further include the ability of an instrument to replicate a stem centralizer. For example, according to one aspect of the present invention, there is provided an instrument for measuring the medullary canal of a resected long bone in order to determine the proper size of a stem centralizer. The instrument includes a contact portion which has a shape substantially similar to the shape of the stem centralizer on the surface opposed to the resected surface of the long bone. Thus, the present invention provides for an instrument which replicates the stem centralizer.

The technical advantages of the present invention further include an instrument that easily passes through the canal to the distal seating position proper for a stem centralizer. For example, according to another aspect of the present invention, there is provided an instrument for measuring the medullary canal of a long bone in order to determine the proper size for a stem centralizer. The instrument includes a contact portion having a contact area for contacting the medullary canal and defines a relief area for providing clearance between the instrument and the medullary canal. Clearance between the portion of the contact portion and canal permits the easy passage of the instrument through the canal and avoids the build-up of pressure at the distal portion of the canal which may prevent the free passage of the instrument. Thus, the present invention provides for an instrument that easily passes through the medullary canal to the distal seating position for the stem centralizer.

The technical advantages of the present invention further include the ability of the instrument of the present invention to be used to assist in selecting the proper size implant for a joint arthroplasty. For example, according to one aspect of the present invention, an instrument for measuring the medullary canal of a long bone is provided. The instrument is used to determine the proper size for a stem centralizer and includes an elongated center portion. A contact portion extends from the center portion and includes a contact area for contacting with the medullary canal. The elongated portion includes a plurality of spaced apart marks or indicia. These marks or indicia when in alignment with the resected portion of the long bone when the contact portion is fully seated in the canal may be used to assist in determining the proper implant to be utilized in the joint arthroplasty. Thus, the present invention provides for an instrument that may be used to assist in the selection of the proper implant for a joint arthroplasty.

The technical advantages of the present invention further include the ability of the instrument of the present invention to be used on any implant stem system. For example, according to one aspect of the present invention an instrument for measuring the medullary canal of a long bone is provided including a central portion and a contact portion extending from the central portion. The contact portion is seated into the medullary canal and the central portion includes marks or indicia which are utilized to assist in determining the proper implant. These marks or indicia in one aspect of the present invention correspond to either a metric or an inch dimension. These metric or inch dimensions may be utilized for any implant system to determine the proper size of the implant to be used. Thus, the present invention provides for an instrument which may be utilized for any implant or stem system for use in joint arthroplasty.

Other technical advantages of the present invention will be readily apparent to one skilled in the art from the following FIGS., descriptions and claims.

BRIEF DESCRIPTION OF THE DRAWINGS

For a more complete understanding of the present invention and the advantages thereof, reference is now made to the following description taken in connection with the accompanying drawings, in which:

FIG. 11 is a plan view of a second end of the instrument of FIG. 7;

FIG. 12 is a top view partially in cross section of FIG. 10 along the line 12-12 in the direction of the arrows;

DETAILED DESCRIPTION OF THE INVENTION

Embodiments of the present invention and the advantages thereof are best understood by referring to the following descriptions and drawings, wherein like numerals are used for like and corresponding parts of the drawings.

Figure 1:
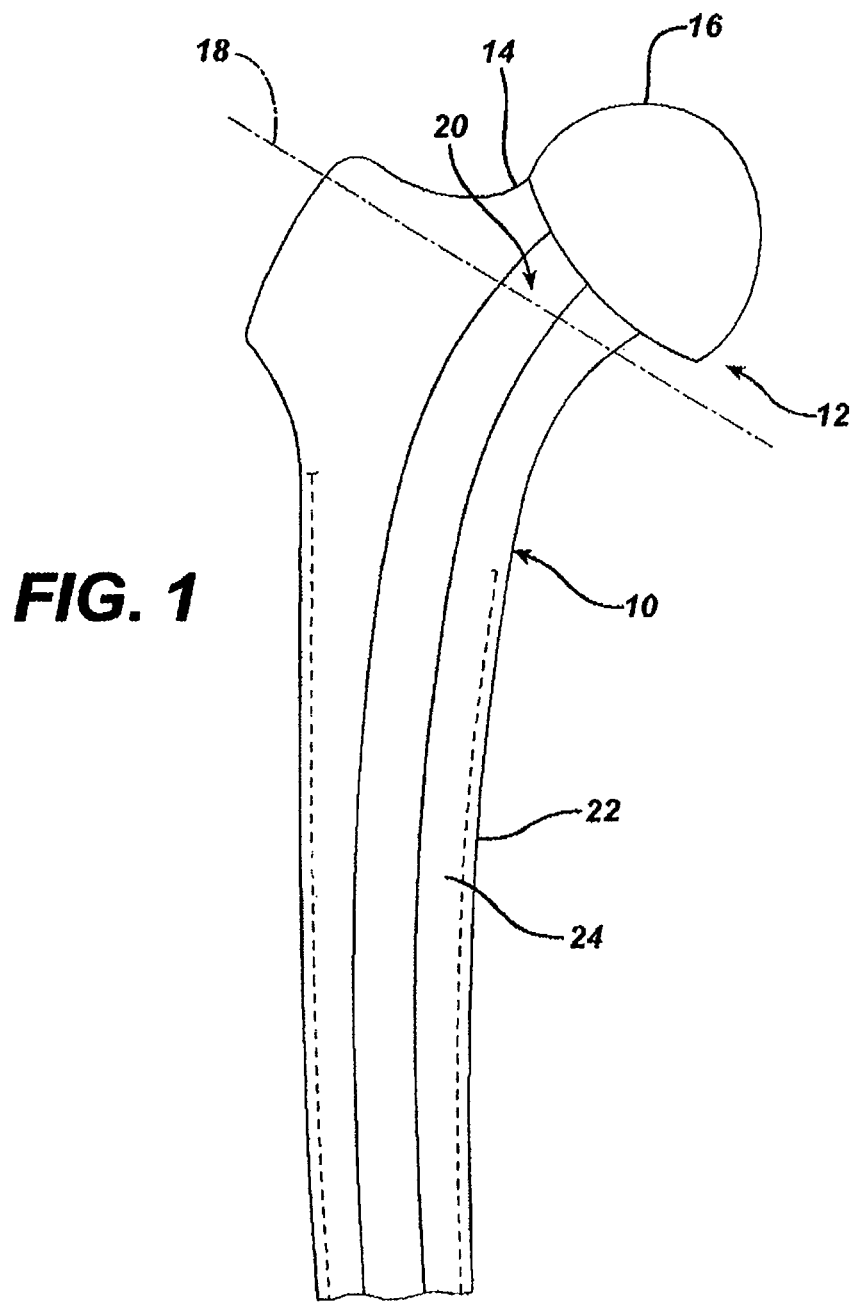
FIG. 1 is a plan view of a resected proximal femur for receiving an instrument in accordance with the present invention.
Figure 1A:
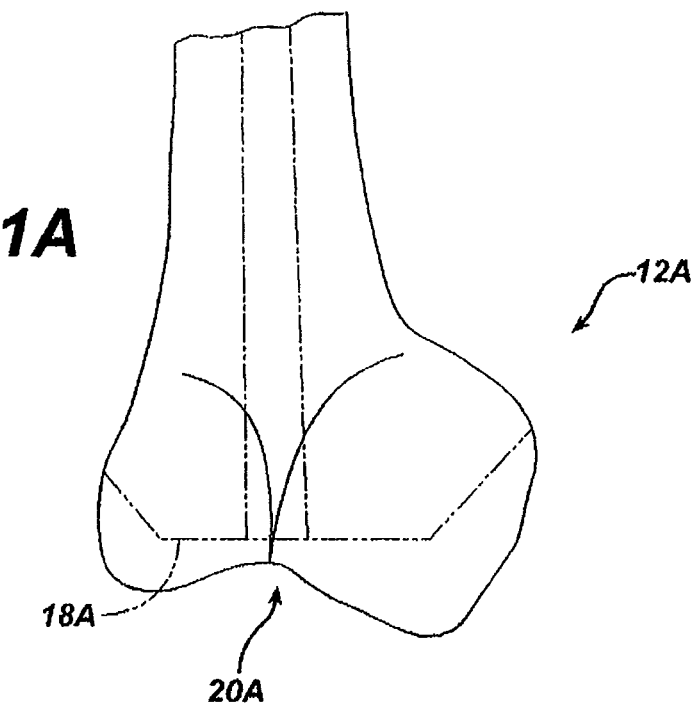
FIG. 1A is a plan view of a resected distal femur for receiving an instrument in accordance with the present invention.

Referring now to FIG. 1, a long bone in the form of femur 10 is shown for use with the instrument of the present invention. The femur 10 includes a proximal portion 12. The proximal portion 12 includes a neck 14 from which a head 16 extends. The head 16 is generally spherical and cooperates with the acetabulum to form a pivoting anatomical joint. When performing joint arthroplasty, the head 16 and neck 14 are resected from the portional proximal femur 12 along resection line 18. The resecting of the proximal femur 12 exposes medullary canal 20 of the femur 10. The femur 10 includes an outer layer of hard dense cortical bone 22 and an inner area of cancellous bone 24 positioned between the cortical bone 22 and the medullary canal 20.

While the instrument of the present invention is particularly well-suited for use in selecting a centralizer or plug for a proximal femur, it should be appreciated that the instrument of the present invention be used in any long bone of the human body, for example and referring now to 1A, the distal femur 12A is shown which includes a medullary canal 20A which is exposed along resection line 18A.

Figure 1B:
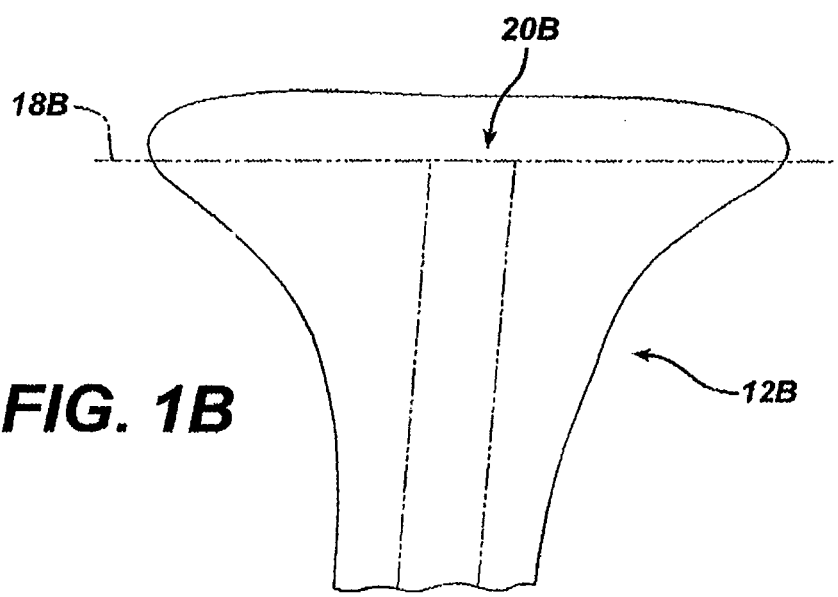
FIG. 1B is a plan view of a resected proximal tibia for receiving an instrument in accordance with the present invention.

Referring that to FIG. 1B, a proximal tibia 12B is shown. The proximal tibia 12B includes a medullary canal 20B which is exposed along resection line 18B.

Figure 1C:
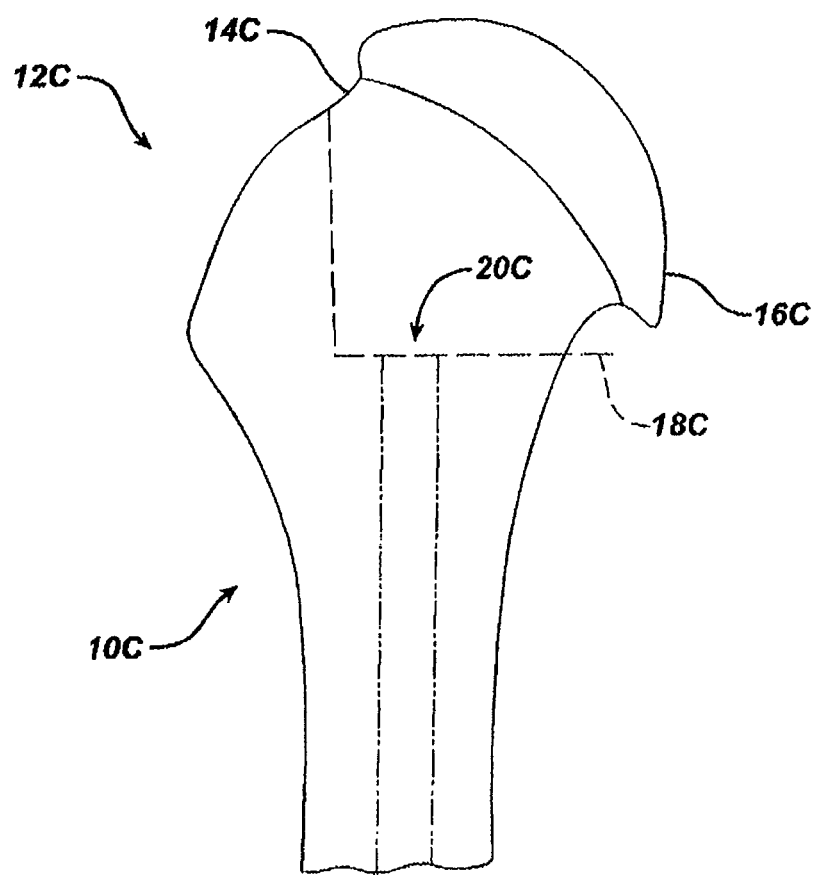
FIG. 1C is a plan view of a resected proximal humerus for receiving an instrument in accordance with the present invention.

Referring now to FIG. 1C a humerus 10C is shown. The humerus 10C includes a proximal portion 12C which includes a neck 14C from which head 16C extends. The humerus 10C is resected along resection line 18C to remove the neck 14C and the head 16C. The resection line 18C exposes medullary canal 20C.

It should be appreciated that the instrument of the present invention may be used with centralizers and plugs to centralize and plug any and all of the medullary canal 20A of the distal femur, the medullary canal 20B of the proximal tibia and the medullary canal 20C of the humerus 10C.

Figure 2:
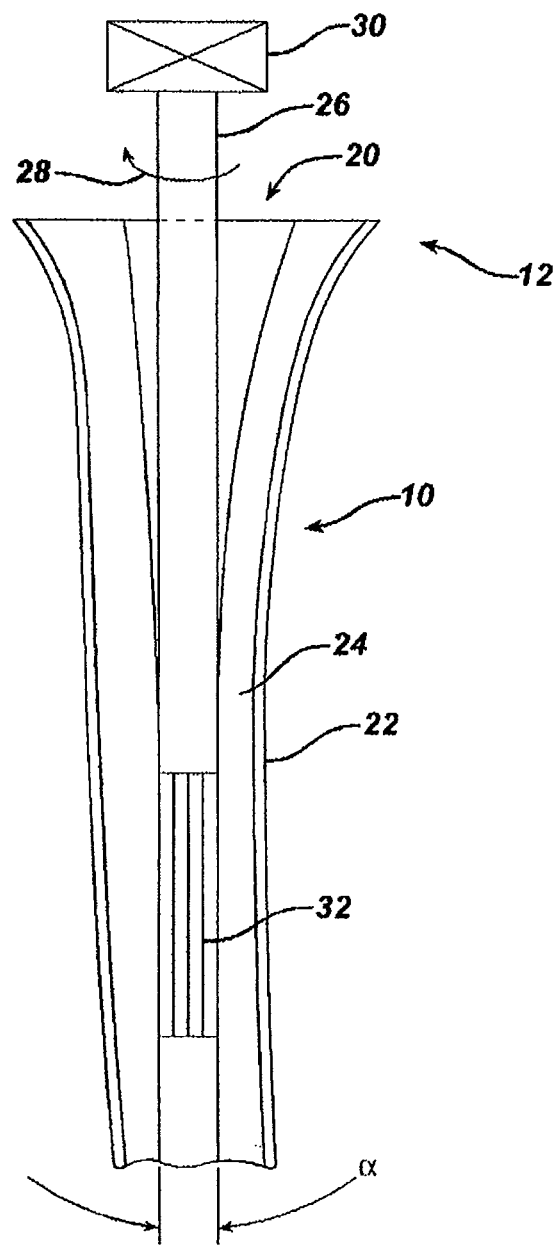
FIG. 2 is a plan view of a proximal femur showing a reamer for use in preparing a cavity for receiving an instrument in accordance with the present invention.

Referring now to FIG. 2, a reamer 26 is shown in position in the medullary canal 20 of the femur 10. The reamer 26 is utilized to open the medullary canal 20 to permit the receiving of the instrument of the present invention. The reamer 26 may be rotated in the direction of arrow 28 by for example power source 30. The power source 30 may be electrical, pneumatic or hydraulic. The reamer 26 may include flutes 32. The flutes 32 may be tapered and may be defined by an included angle a. The angle a also defines the angle of the tapered opening of the medullary canal 20 for receiving the instrument of the present invention.

Figure 3:
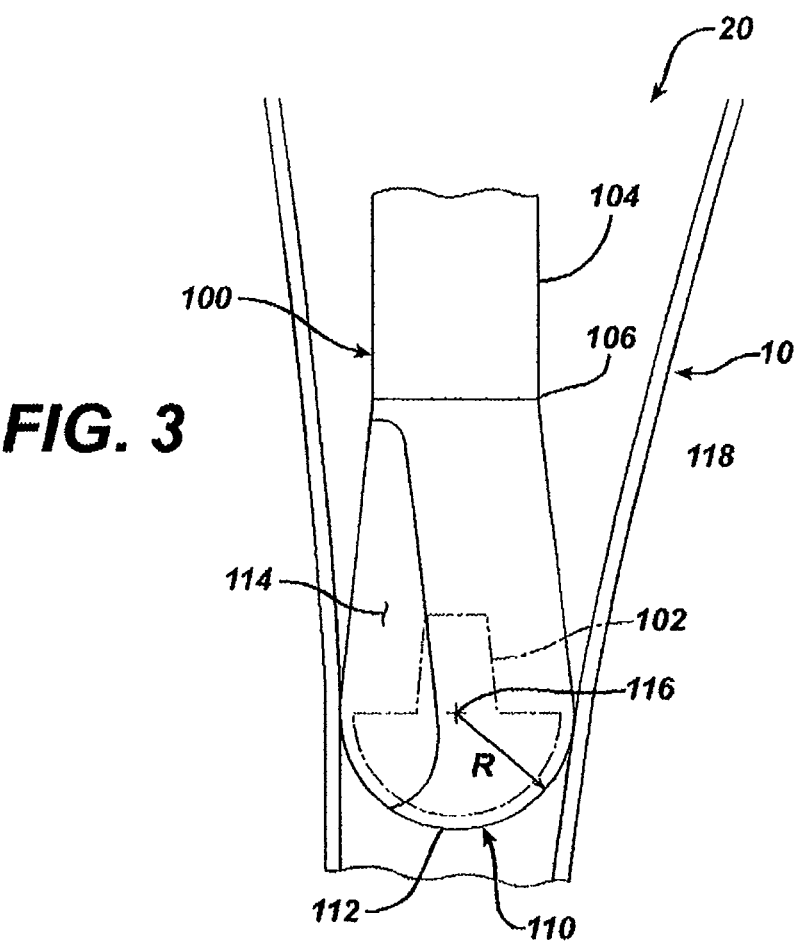
FIG. 3 is a plan view of an instrument in accordance with an embodiment of the present invention showing an instrument having a contact portion with a relief area.
Figure 3A:
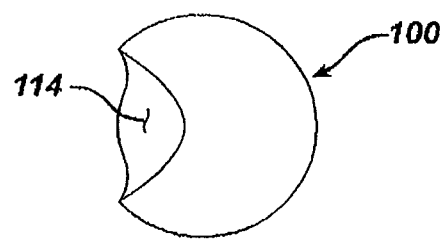
FIG. 3A is a bottom view of the instrument of FIG. 3.
Figure 3B:
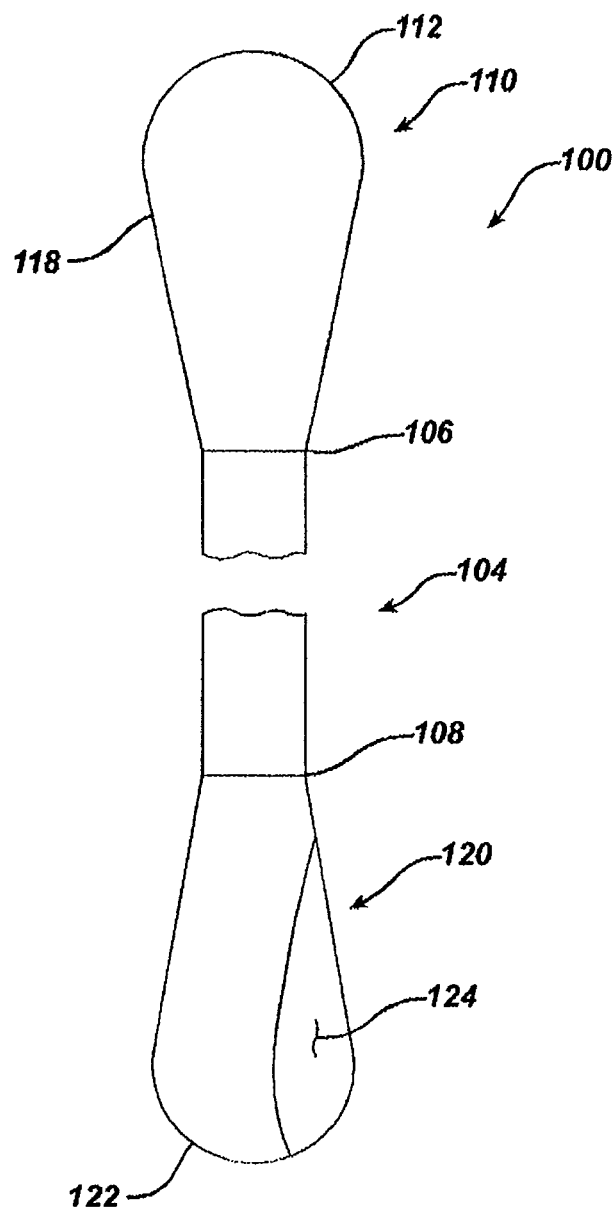
FIG. 3B is an end view of the instrument of FIG. 3.

Referring now to FIGS. 3, 3A and 3B, and embodiment of the present invention is shown as instrument 100. The instrument 100 is used for measuring the medullary canal 20 of the long bone 10 in order to determine the proper size for a canal implant 102. It should be appreciated that canal implant 102 may be for example, a stem centralizer or a cement plug. The instrument 100 includes an elongated central portion 104 defining opposed first end 106 and second end 108. The instrument 100 further includes a contact portion 110 extending from the first end 106 of the elongated central portion 104 of the instrument 100. The contact portion 110 includes a contact area 112 for contact with the medullary canal 20 and defines a relief area 114 for providing clearance between the instrument 100 and the medullary canal 20.

The elongated central portion 104 may have any suitable shape capable of supporting the contact portion 110 of the instrument 100. For example, the elongated central portion may have a uniform cross-section. The uniform cross-section of the said proportion 104 may have any shape, for example triangular, rectangular, or may have as shown in FIGS. 3, 3A & 3B the circular saw cross-section providing for a cylindrical elongated central portion 104.

The contact portion 110 may have any suitable shape and may, for example, provide for a contact area 112 which is arcuate. The arcuate contact area 112 of the contact portion 110 of the instrument 100 may assist in the insertion of the instrument 100 into the canal 20. The contact area 112 may be defined by example a radius R extending from origin 116 providing, for example, for contact area 112 to be generally hemispherical. The contact portion 110 adjacent first end 106 of the central portion 104 may have any suitable shape and may be arcuate or as shown in FIGS. 3, 3A, and 3B be generally conifrustrical. The connecting portion 118 and the contact area 112 of the contact portion 110 may have for example, a shape which is generally pear shaped.

The relief area 114 of the contact portion 110 may have any shape, and may for simplicity be generally planar.

As shown in FIG. 3B, the instrument 100 may further include a second contact portion 120 extending from the second end 108 of the elongated center portion 104. The second contact portion 120 may have a contact area 122 for contact with the medullary canal 20 and may define a relief area 124 for providing clearance between the instrument 100 and the medullary canal 20. The second contact portion 120 as shown in FIG. 3B may be similar in size and shape to the first contact portion 110. The second contact portion 120 may be slightly larger or smaller than the first contact portion 110 and be utilized to replicate a canal implant that is either slightly larger or slightly smaller than the canal implant for which the first contact portion 110 is designed.

The instrument 100 may be made of any suitable durable material and may for simplicity be of a one-piece or integral construction. It should be appreciated, however, that the instrument 100 may be modular having, for example, contact portions 110 and 120 being made of a separate component from the central portion 104. The instrument 100 may be made of any suitable durable material capable of use in a surgical procedure. Preferably, the instrument 100 may be made of a material that is either disposable or capable of being sterilized by standard sterilization techniques. For example, the instrument 100 may be made of a plastic or a metal. If made of a metal, the instrument 100 may be made of for example, cobalt chromium alloy, stainless steel alloy, or titanium alloy.

Figure 4:
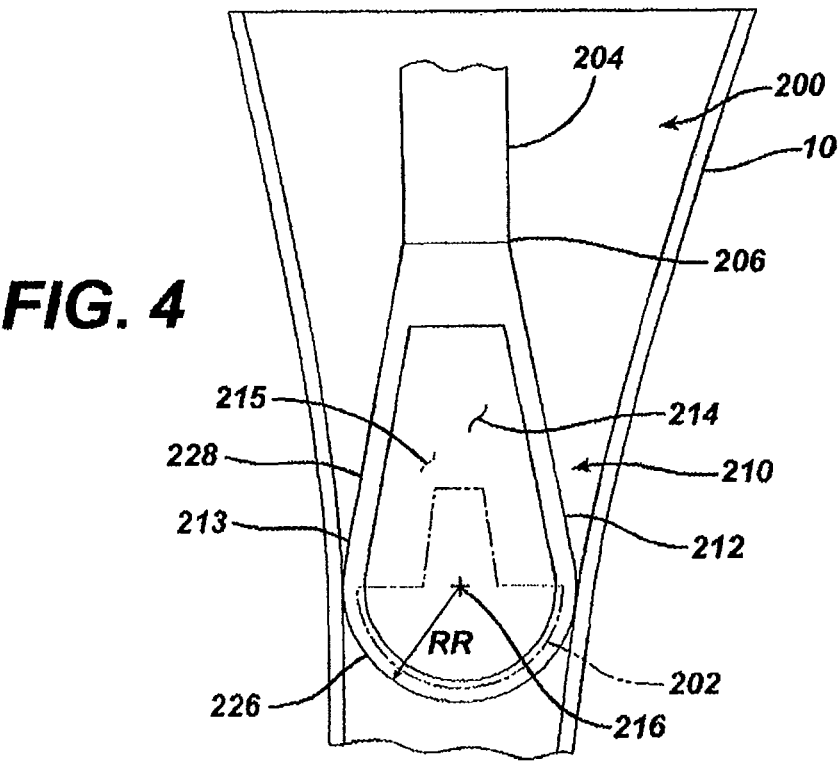
FIG. 4 is a plan view of an instrument in accordance with another embodiment of the present invention showing an instrument having a pair of spaced apart contact portions with a pair of spaced apart relief areas.
Figure 4A:
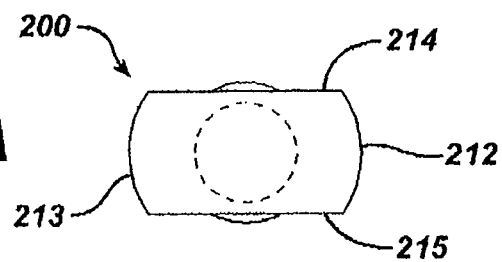
FIG. 4A is a bottom view of the instrument of FIG. 4.
Figure 4B:
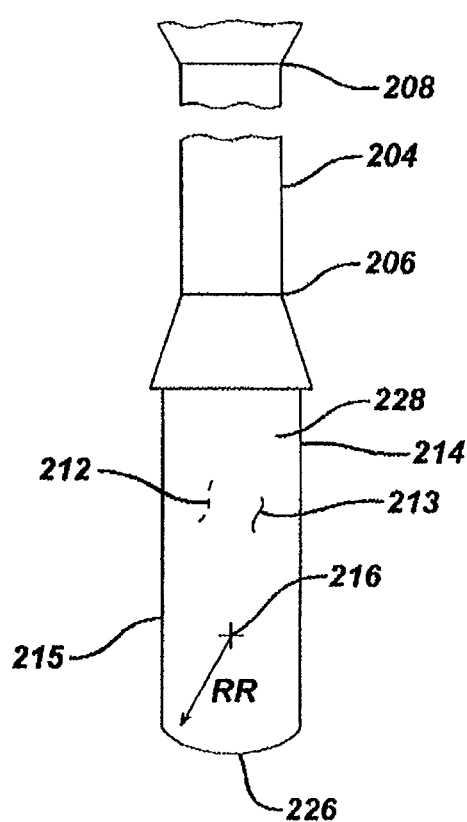
FIG. 4B is an end view of the instrument of FIG. 4.

Referring now to FIGS. 4, 4A and 4B, another embodiment of the present invention is shown as instrument 200. Similar to the instrument 100 of FIGS. 3, 3A, and 3B, the instrument 200 of FIGS. 4, 4A and 4B is utilized for measuring the medullary canal 20 of a long bone 10 in order to determine the proper size for a canal implant. The instrument 200 is utilized for determining the proper size of a canal implant 202. Canal implant 202 may be in the form of, for example, a stem centralizer or a plug. Similar to the instrument 100 of FIG. 3, the instrument 200 of FIG. 4 includes an elongated central portion 204 defining a first end 206 and an opposed second end 208.

Further similar to the instrument 100, the instrument 200 includes a contact portion 210 extending from the first end 206 of the elongated central portion 204. The contact portion 210 of the instrument 200 of FIGS. 4, 4A, and 4B is different than the contact portion 110 of the instrument 100 in that the contact portion 210 includes a plurality of contact areas. For example, the contact portion 210 includes a first contact area 212 and a second contact area 213. The contact areas 212 & 213 provide for contact with the medullary canal 20 of the long bone 10. The contact portion 210 further defines a plurality of relief areas. For example, the contact portion 210 defines a first relief area 214 as well as a second relief area 215. The relief areas 214 & 215 provide clearance between the instrument and the medullary canal 20. Relief areas 214 & 215 provide for an easier and smoother insertion of the instrument 200 into the canal 20 as well as avoid pressure caused by the insertion of the instrument 200 that may prevent the proper seating of the instrument 200 in the canal 20.

The central elongated portion 204 of the instrument 200 may have any suitable shape and may, for simplicity, be cylindrical. The contact portion 210 as shown in FIG. 4 includes the first and second contact areas 212 & 213 as well as the first and second relief portions 214 & 215, respectively. It should be appreciated that the relative size of the relief areas 214 & 215 as well as the contact areas 213 & 214 should be selected to provide for a proper seating of the instrument 200 into the canal 20 as well as to provide for ease of insertion of the instrument 200 into the canal 20.

For example, as shown in FIG. 4, the relative portion of the contact portion 210 in relief and in contact may for example be roughly equal. Also, the first contact area 212 and the second contact area 213 may have a similar size and for simplicity, may have a similar shape. Similarly, the first relief area 214 and the second relief area 215 may have similar sizes and may for simplicity have a similar shape.

The first and second contact areas 212 & 213 may have any suitable shape, and may as shown in FIGS. 4, 4A and 4B be generally arcuate. The contact portion 210 may include a generally hemispherical end portion 226 and a generally conifrustrical intermediate portion 228. The hemispherical end portion 226 may be defined by example, by radius RR extending from origin 216. The first relief area 214 and the second relief area 215 may for simplicity be plainer and may as shown in FIGS. 4A and 4B the first relief area 214 may be parallel in space from the second relief area 215.

It should be appreciated that the instrument 200 may include a second contact portion similar to the contact portion 210 but preferably may be slightly larger or smaller than the contact portion 210. The second contact portion not shown may for example extend from second end 208 of the central portion 204 of the instrument 200.

Similar to the instrument 100 of FIG. 3, the instrument 200 of FIG. 4 may be integral or modular and be made of any suitable durable material, such as those described with respect to instrument 100.

Figures 5, 5A:
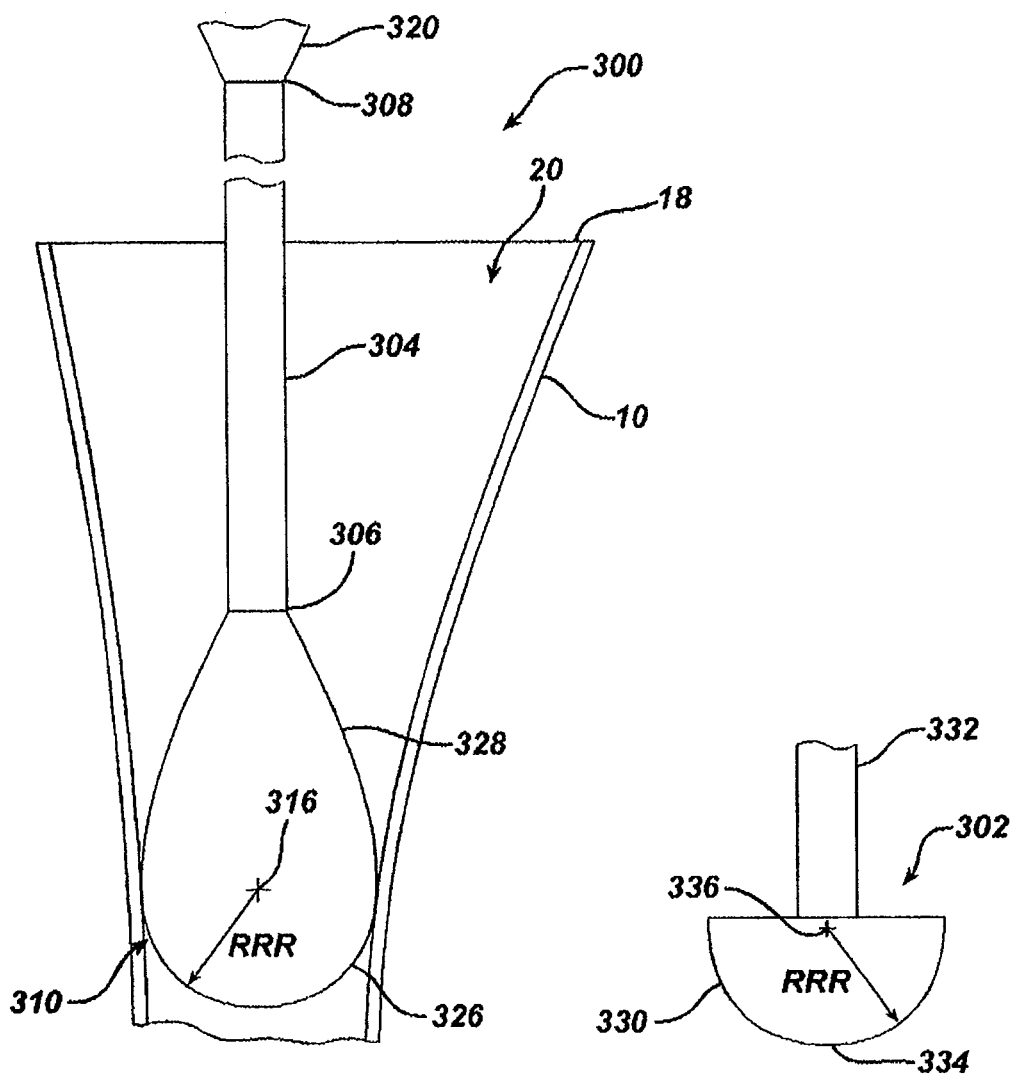
FIG. 5 is a plan view of an instrument in accordance with yet another embodiment of the present invention showing an instrument having a part of the contact portion similar to the distal end of a corresponding centralizer.
FIG. 5A is a plan view of the corresponding centralizer for use with the instrument of FIG. 5.

Referring now to FIG. 5, another embodiment of the present invention is shown as instrument 300. The instrument 300 is utilized for measuring the medullary canal 20 of a resected long bone 10 in order to determine the proper size of a canal implant. For example, one such canal implant is a stem centralizer 302 (see FIG. 5A). The instrument 300 includes an elongated central portion 304 which includes a first end 306 and an opposed second end 308.

The instrument 300 further includes a contact portion 310 extending from the first end 306 of the elongated central portion 304 of the instrument 300. The contact portion 310 has a shape substantially similar to the shape of the stem centralizer 302 (see FIG. 5A) on the surface of the instrument 300 opposed to the resected surface 18 of the long bone 10.

The elongated central portion 304 may have a shape similar to for example the elongated portion central portion 104 of the instrument 100 of FIG. 3.

The contact portion 310 may include an end contact area 326 opposed to the resection line 18. The end contact area 326 may have any suitable shape and may be arcuate. For example, the end contact area 326 may as shown in FIG. 5 be generally hemispherical and defined by radius RRR extending from center point 316. The contact portion 310 may further include an intermediary contact area 328 extending from the end contact area 326 to the first end 306 of the elongated central portion 304.

Referring now to FIG. 5A, stem centralizer 302 for use with the instrument 300 is shown in greater detail. The stem centralizer 302 includes a contact portion 330 as well as an opposed stem 332. The contact portion 330 includes a periphery 334 defined by radius RRR extending from center point 336. The radius RRR of the centralizer 302 is the same as the radius RRR of the contact portion 326. The instrument 300 replicates the shape of the periphery 334 of the centralizer 302.

Referring again to FIG. 5, the instrument 300 may further include a second contact portion 320 similar to contact portion 310. The second contact portion 320 may extend outwardly from second end 308 of the elongated central portion 304 of the instrument 300.

The instrument 300 may be made of any suitable durable material and may be made of a plastic or a metal. Preferably the instrument 300 is made of material that may be sterilized by any commercially available sterilization technique. The instrument 300 may be a plastic or a metal. If made of a metal the instrument 300 may be made of cobalt chromium alloy, titanium alloy or stainless steel alloy. The instrument 300 may be integral or may be modular.

Figures 6, 6A:
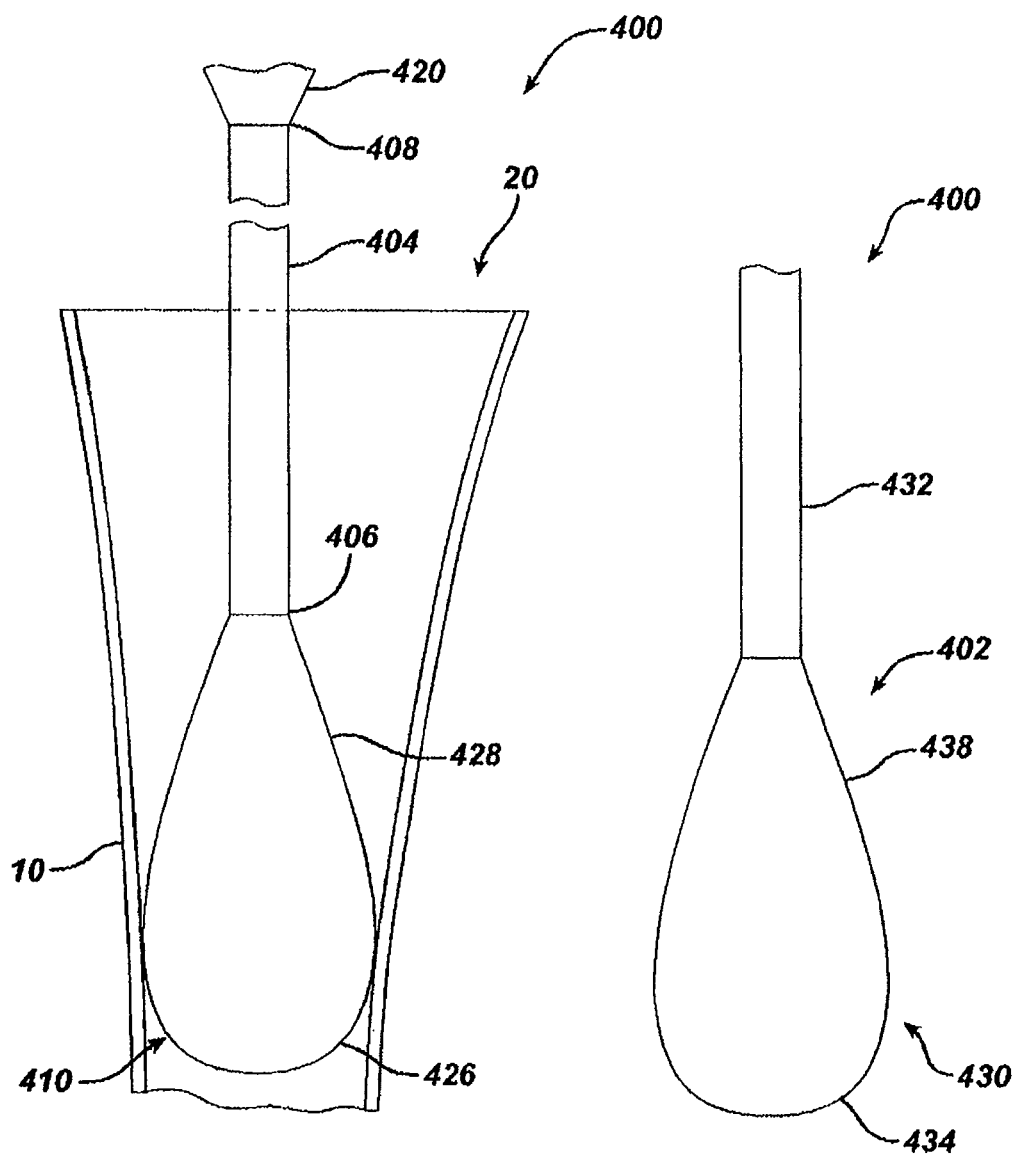
FIG. 6 is a plan view of an instrument in accordance with yet another embodiment of the present invention showing an instrument having a contact portion similar to the distal end of a corresponding centralizer.
FIG. 6A is a plan view of the corresponding centralizer for use with the instrument of FIG. 6.

Referring now to FIG. 6 another embodiment of the present invention is shown as instrument 400. Instrument 400 is similar to instrument 300 and includes an elongated central portion 404. The central portion 404 includes a first end 406 and an opposed second end 408. A contact portion 410 extends outwardly from first end 406 of the central portion 404.

Contact portion 410 of the instrument 400 has a shape designed to replicate contact portion 430 of the stem centralizer 402 (see FIG. 6A). For example, the contact portion 410 includes an end contact area 426 as well as an intermediate contact area 428 positioned between the end contact area 426 and first end 406 of the central portion 404 of the instrument 400.

Similarly, referring to FIG. 6A, the contact portion 430 of the centralizer 402 includes an end contact area 434 as well as an intermediary contact area 438 positioned between the end contact area 434 and stem portion 432 of the centralizer 402.

Referring again to FIG. 6, the instrument 400 may have any suitable size and shape and may, similar to the instrument 100 of FIG. 3, include a second contact portion 420 extending from second end 408 of the instrument 400.

The instrument 400 may be made of any suitable durable material and may for example be made of a metal or a plastic. Preferably the instrument 400 is made of a material that may be sterilized by conventional sterilization techniques. The instrument 400, if made of a metal, may be made of, for example, cobalt chromium alloy, stainless steel alloy or titanium alloy. The instrument 400 may be integral or may be modular.

Figure 7:
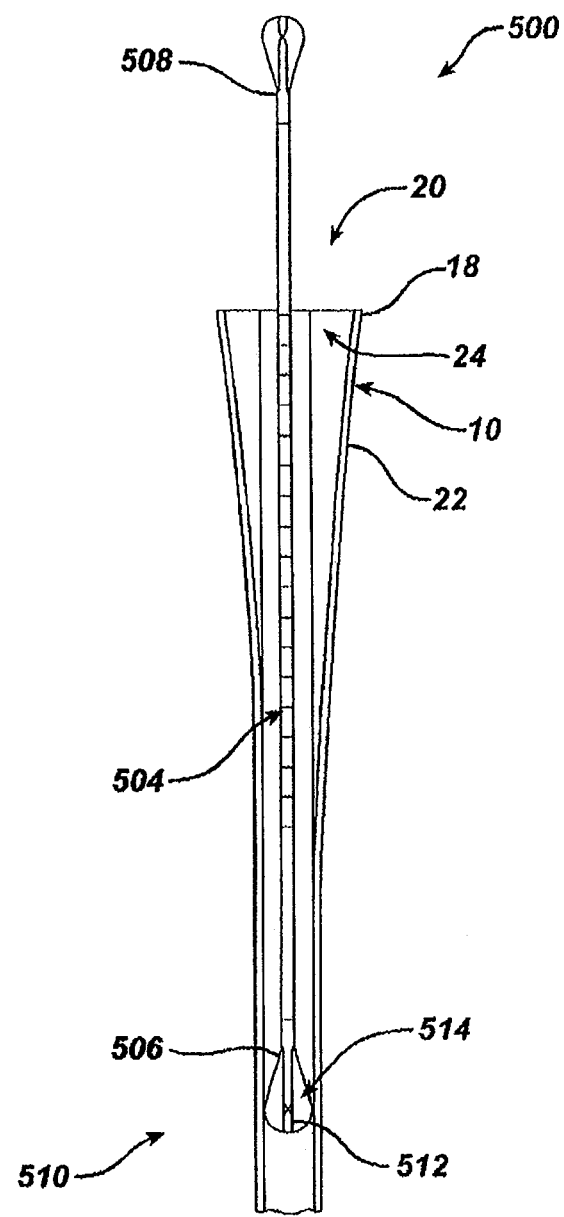
FIG. 7 is a plan view of an instrument in accordance with yet another embodiment of the present invention with a portion of the instrument in position in the cavity of a proximal femur.

Referring now to FIG. 7 another embodiment of the present invention is shown as instrument 500. The instrument 500 is utilized for measuring the medullary canal 20 of the long bone 10 in order to determine the proper size for a canal implant, for example a stem centralizer. The instrument includes an elongated central portion 504. The central portion 504 includes a first end 506 and an opposed second end 508. Contact portion 510 extends from the first end 506 of the elongated central portion 504. The contact portion 510 has a contact area 512 for contact with the canal and defines a relief area 514 providing clearance for the instrument 500 in the medullary canal 20.

Figure 8:
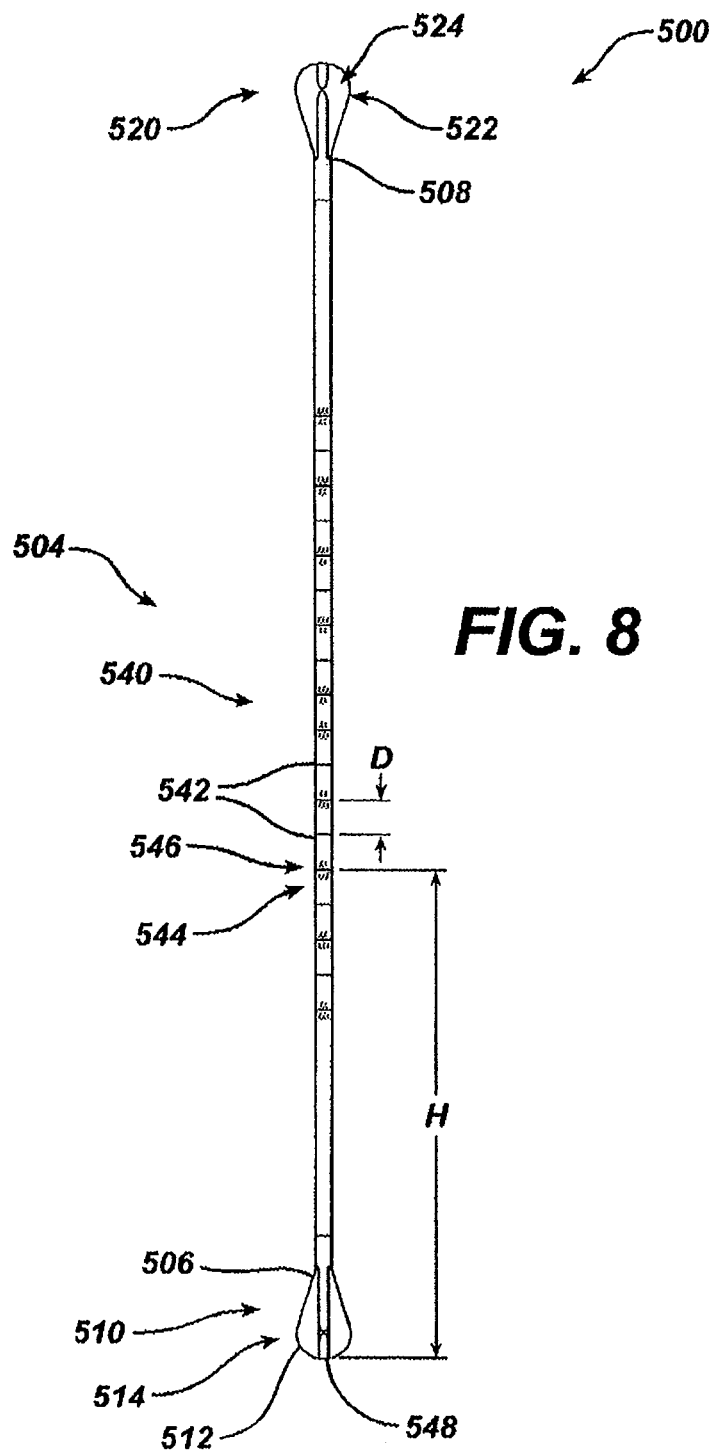
FIG. 8 is a plan view of the instrument of FIG. 7.

Referring now to FIG. 8, the instrument 500 is shown in greater detail. As shown in FIG. 8, the instrument 500 further includes a second contact portion 520 extending outwardly from second end 508 of the central portion 504 of the instrument 500. The second contact portion 520 like the first contact portion 510 includes contact area 522 as well as relief area 524.

Preferably as shown in FIG. 8, the elongated central portion 504 includes indicia 540. The indicia 540 is utilized to determine the position of the contact portions 510 & 520 with respect to resection line 18 of the femur 10 (see FIG. 1). The indicia 540 may include a plurality of spaced apart marks 542. The marks 542 may provide a visual reference for alignment with the resection line 18 (see FIG. 7). The marks 542 may be spaced apart a distance of for example ten millimeters. The marks 542 may thus correspond to an inch or metric dimension. For example ten millimeters is shown in the instrument 500 of FIG. 8.

The indicia 540 may further include numerical markings 544 and alphabetical markings 546. The numerical markings 544 may correspond to a particular dimension. For example, a metric dimension from the resection line 18 to the contact portion 510 or 520 of the instrument 500. For example, as shown in FIG. 8, the reference numeral 140 may be spaced a distance H from end 548 of the first contact portion 510. As shown in FIG. 8 the dimension H is 140 millimeters.

It should be appreciated that in order for the indicia 540 to be easily read by the surgeon the numeral 140 is shown upside down so that the surgeon may read the dimension when the instrument 500 is inserted into the medullary canal 20 of the long bone 10. The indicia 540 may be placed on the central portion 504 of the instrument 500 by any suitable method, for example by stamping, printing, or etching.

Figure 9:
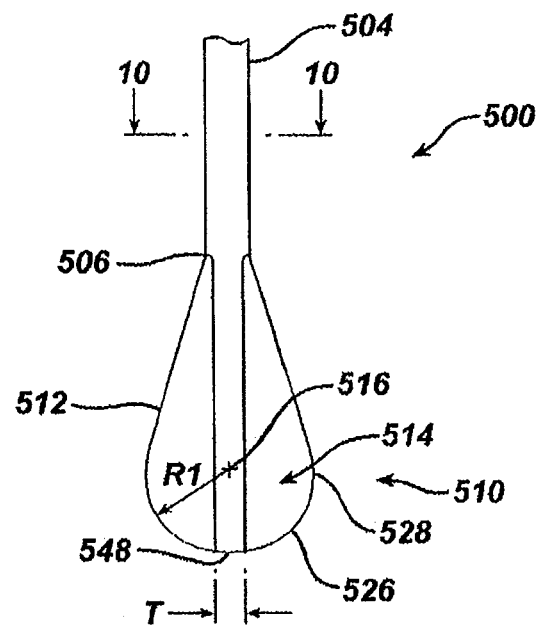
FIG. 9 is a plan view of a first end of the instrument of FIG. 7.
Figure 10:
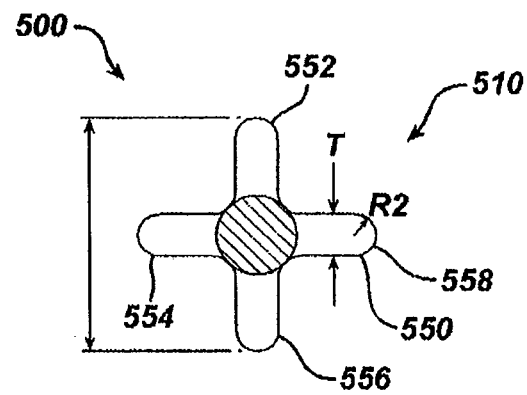
FIG. 10 is a top view partially in cross section of FIG. 9 along the line 10-10 in the direction of the arrows.

Referring now to FIGS. 9, 10, 11 and 12 the first contact portion 510 and second contact portion 520 of the instrument 500 are shown in greater detail. Referring now to FIGS. 9 and 10, first contact portion 510 of the instrument 500 is shown in greater detail. As shown in FIG. 9, the first contact portion includes a contact area 512 as well as a relief area 514. The contact area 512 as shown in FIG. 9 may include an end contact area 526 extending from end 548 of the first contact portion 510. The end contact area 526 may be of any suitable shape and may for simplicity and to best replicate the shape of the centralizer 502 (see FIG. 13) may have a generally hemispherically shape defined by a radius R1 extending from center point 516.

The first contact portion 510 may also include an intermediate contact area 528 extending from the first contact area 526 to the first end 506 of the central portion 504 of the instrument 500. The intermediate contact area 528 may have any suitable shape and for simplicity as shown in FIG. 9 may be generally conifrustrical.

While the instrument of the present invention may include a solitary relief area and a solitary contact area as shown in FIG. 10, the instrument 500 may include a plurality of spaced apart contact areas as well as a plurality of spaced apart relief areas.

Relief areas and contact areas may be equally spaced about the perimeter of the instrument 500 and may include for example 2, 3, 4, 5, 6, 7, or 8 or more alternating relief areas and alternating contact areas. For example as shown in FIG. 9, the instrument 500 may include four relief areas and four contact areas. Each of the contact areas, for example contact area 550, may have a uniform thickness of, for example, thickness T.

Referring to FIG. 10, first contact portion 510 is shown in greater detail with the plurality of contact areas and relief areas shown more clearly. For example, the first contact portion includes the first contact area 550, the second contact area 552, third contact area 554 and fourth contact area 556. Each of the contact areas 550, 552, 554, 556 have an identical thickness of, for example, thickness T. The outer portion 558 of the contact portions 550, 552, 554, 556 may be arcuate and defined by a radius R2.

Referring now to FIGS. 11 and 12, the second contact portion 520 of the instrument 500 is shown in greater detail. The second contact portion 520 extends from second end 508 of the central portion 504. The second contact portion 520 includes an end contact area 560 as well as an intermediate contact area 562. The end contact area 560 may have any suitable shape and may for simplicity have a shape similar to that of the corresponding centralizer. For example the end contact area 560 may be generally hemispherical and defined by a radius R3 extending from center point 564.

The intermediate contact area 562 may have any shape and may for simplicity be conifrustrical extending from the end contact area 560 to the second end 508 of the central portion 504 of the instrument 500. The contact areas, for example contact area 565, may have any suitable thickness and may have a uniform thickness of for example T-2. The thickness T-2 may be similar to the thickness T of the contact area 512 of the first contact 510.

The second contact portion 520 may be similar to the first contact portion 510 and may include a plurality of contact areas and a plurality of relief areas. The contact areas and relief areas may be symmetrically positioned about the instrument 500. For example the second contact portion 520 may include 2, 3, 4, 5, 6, 7, 8, 9, or 10 or more spaced apart contact areas as well as a corresponding number of spaced apart relief areas. As shown in FIG. 12, the second contact portion 520 may include a first contact area 565, a second contact area 566, a third contact area 568 and a fourth contact area 570.

As shown in FIG. 12, the first contact area 565 may for simplicity have a uniform thickness T-2 and have an end 572 which is generally arcuate. For example, the end 572 may be generally semi-circular and defined by a radius R3. It should be appreciated that the second contact area 566, the third contact area 568 and the fourth contact area 570 may be substantially the same as the first contact area 565 and have end portions which are generally hemispherical.

Figure 13:
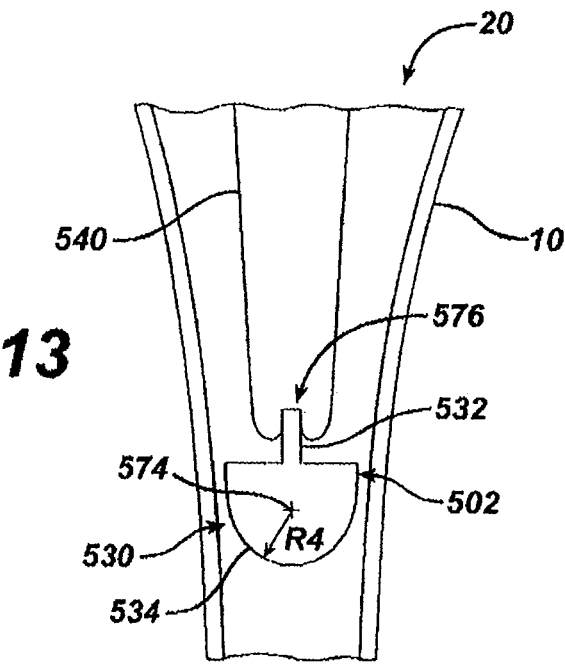
FIG. 13 is a plan view partially in cross section of the instrument of FIG. 7 showing the first end of the instrument in position in the cavity of the proximal femur.
Figure 14:
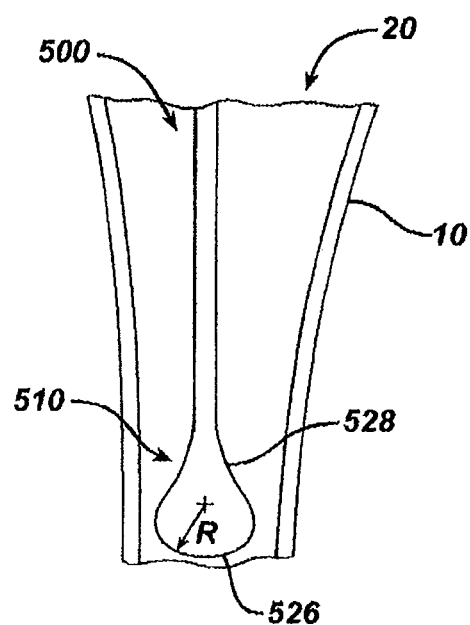
FIG. 14 is a plan view partially in cross section of the instrument of FIG. 7 showing the second end of the instrument in position in the cavity of the proximal femur.

Referring now to FIG. 13 and FIG. 14, the end contact area 534 of the stem centralizer 502 is shown in the medullary canal 20 of the long bone 10 having a shape generally the same as the end contact area 526 of the instrument 500.

Referring now to FIG. 13, the stem centralizer 502 has a contact portion 530 for contact with the medullary canal 20 of the long bone 10. The contact portion 530 of the stem centralizer 502 is designed to have the shape similar to the end contact area 526 of the first contact portion 510 of the instrument 500.

It should be appreciated that the instrument 500 may also include the second contact portion 520 for use with a stem centralizer not shown having a different size. The contact portion 530 of the stem centralizer 502 includes an end contact portion 534 defined by a radius R4 extending from centerline 574 stem centralizer 502 further includes a stem 532 which matingly fits with opening 576 in implant 540.

Referring now to FIG. 14, the instrument 500 is shown inserted in medullary canal 20 of the long bone 10. The instrument 500 includes the end contact area 526 formed in the distal part of first contact portion 510 of the instrument 500.

Figure 15:
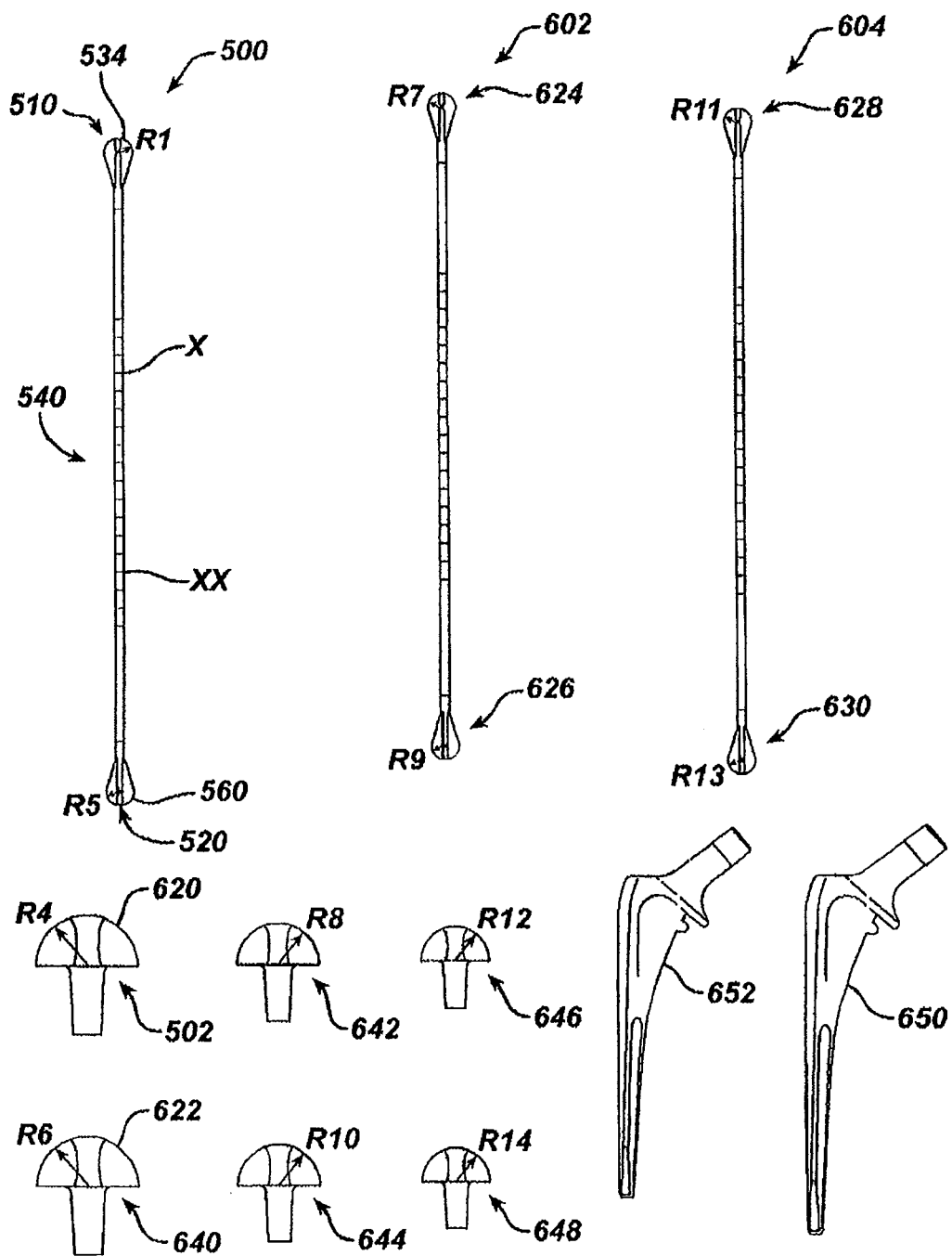
FIG. 15 is a plan view of an instrument kit according to another embodiment of the present invention including the instrument of FIG. 7 as well as a second instrument and a third instrument, the second instrument and the third instrument being similar to the first mentioned instrument, but having end portions of different sizes.

Referring now to FIG. 15 another embodiment of the present invention is shown as kit 600. The kit 600 is for use in performing total hip arthroplasty. The kit includes a plurality of instruments. Each of the instruments is adapted for measuring the medullary canal 20 of a femur 10. Kit 600, as shown in FIG. 15, includes a first instrument 500 and a second instrument 602. It should be appreciated that the instrument 500 may optionally include a third instrument 604.

The kit 600 further includes a plurality of centralizers. For example as shown in FIG. 15 the kit 600 includes a first centralizer 502 and a second centralizer 640. It should be appreciated that the kit 600 may include additional centralizers. For example, and as shown in FIG. 15, the Kit 600 may include a third centralizer 642 a fourth centralizer 644, a fifth centralizer 646 as well as a sixth centralizer 648.

Kit 600 may further include a hip stem 650 for use with one of the stem centralizers, for example first stem centralizer 502. It should be appreciated that the Kit 600 may include a second hip stem 652.

As shown in FIG. 15, the kit 600 may be adapted such that each of the instruments, 500, 602, 604 has at least one dimension different than each of the other instruments. It should also be appreciated that the kit 600 can also be adapted such that each of the stem centralizers, for example stem centralizer 502, 640, 642, 644, 646 and 648 may each have a unique dimension. Further, the Kit 600 may be adapted such that each of the hip stems, for example hip stem 650 and hip stem 652 may each have a unique dimension. It should be appreciated by providing the plurality of instruments, centralizers and stems, a system may be provided to accommodate a wide variety of patient needs.

For example, as shown in FIG. 15, the instrument 500 includes a first contact portion 510 having an end contact area 534 which has dimensions similar to end contact area 620 of the first stem centralizer 502. Similarly, the instrument 500 may include a second contact portion 520 having an end contact area 560 having dimensions similar to end contact area 622 of the second stem centralizer 640. Thus the instrument 500 has a first contact portion 510 for use with selecting the first stem centralizer 502 and a second contact portion 520 for use in selecting the second stem centralizer 640. Similarly, the instrument 602 includes a first contact portion 624 for use in selecting the third stem centralizer 642 and a second contact portion 626 for use in selecting the fourth stem centralizer 644. As shown in FIG. 15 the first contact portion 510 includes a radius R1 which is similar to the radius R4 of the first stem centralizer 502. The second contact portion 520 of the instrument 500 includes a radius R5 which is similar to the radius R6 of the second stem centralizer 640. The first contact portion 624 of the instrument 602 includes a radius R7 which is similar to the radius R8 of the third stem centralizer 642. The second contact area 626 of the second instrument 602 includes a radius R9 which is similar to the radius R10 of the fourth stem centralizer 644. The third instrument 604 includes a first contact portion 628 which includes a radius R11 which is similar to the radius R12 of the fifth stem centralizer 646 and a second contact portion 630 which has a radius R13 similar to the radius R14 of the sixth stem centralizer 648.

The first contact portion 624 of the second instrument 602 corresponds with the use of the third stem centralizer 642 while the second contact portion 626 of the second instrument 602 corresponds with the use of the fourth stem centralizer 644. Similarly, the first contact portion 628 of the third instrument 604 corresponds to the use of the fifth stem centralizer 646 while the second contact portion 630 of the third instrument 604 corresponds to the use of the sixth stem centralizer 648.

The position of the instrument, for example instrument 500 in the canal 20 of the long bone 10 may be utilized to determine which of a variety of hip stems are proper for a particular patient. For example the instrument may include the indicia 540. Each position on the indicia 540 may represent the use of a particular stem. For example and as shown in FIG. 15, if the resection line 18 of the femur 10 corresponds to position x, for example, the first hip stem 650 should be selected. Alternatively, if the resection line 18 of the hip stem 10 corresponds to position XX, the second hip stem 652 should be utilized.

Figure 16:
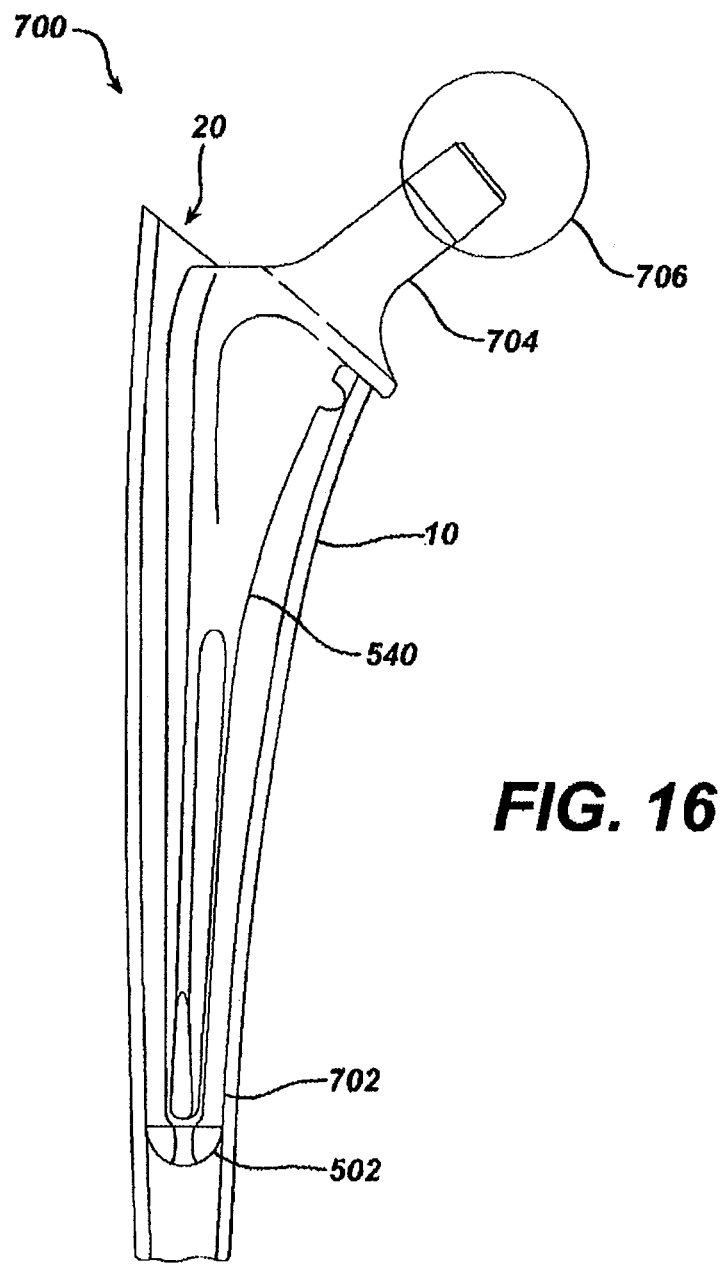
FIG. 16 is a plan view of a prosthesis for use with the instrument of FIG. 7.

Referring now to FIG. 16, a hip stem in the form of for example stem 540 is shown in use in the medullary canal 20 of the stem 10. The implant 540 includes a stem centralizer 502 connected to distal portion 702 of the implant 540. The implant 540 may also include a neck 704 to which a head 706 is attached.

Figure 17:
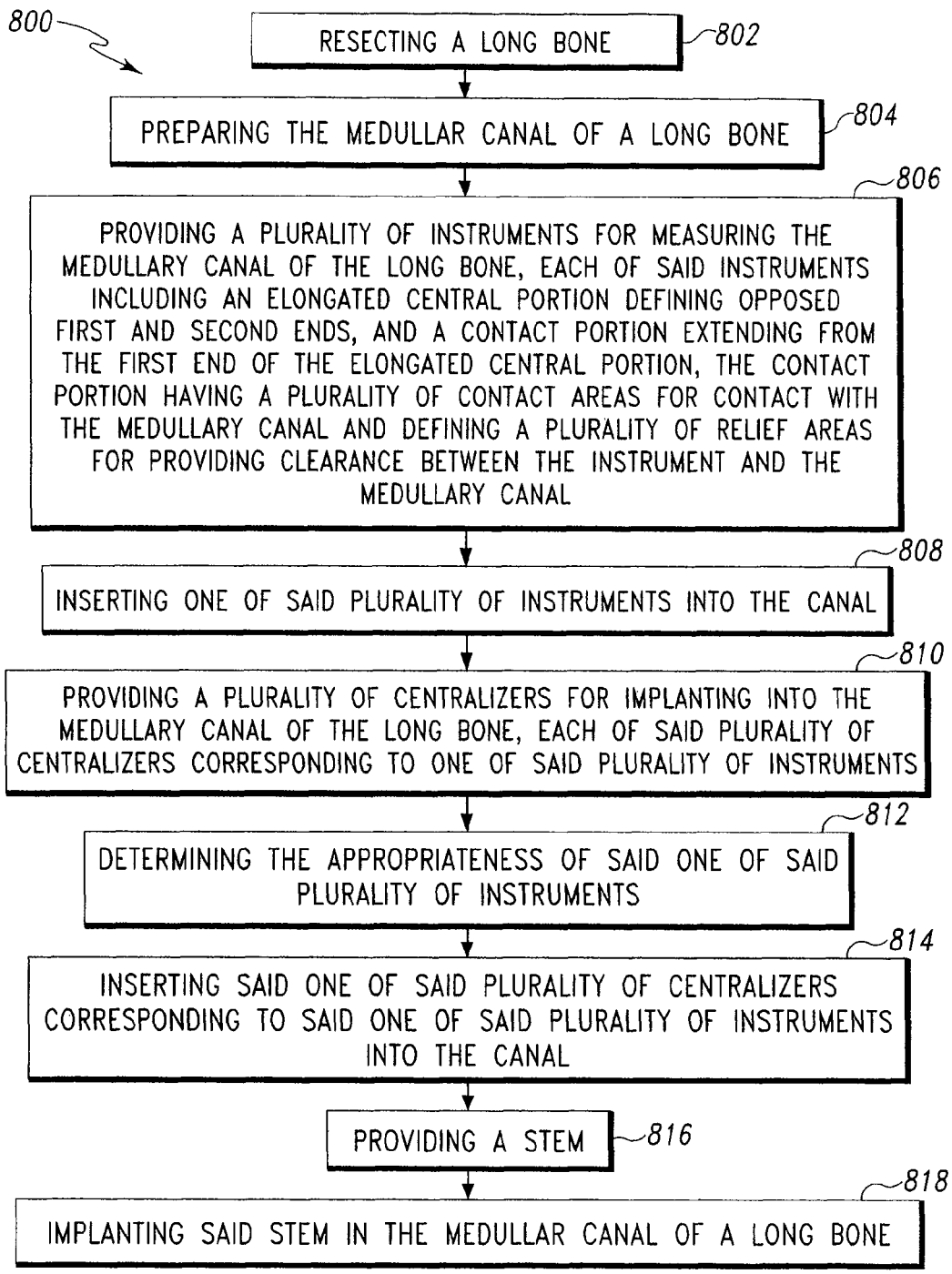
FIG. 17 is a flow chart of a method for performing total joint arthroplasty in accordance with an embodiment of the present invention.

Referring now to FIG. 17, another embodiment of the present invention is shown as method 800. Method 800 includes a first step 802 of resecting a long bone and a second step 804 of preparing the medullary canal of a long bone. The method 800 further includes a third step 806 of providing a plurality of instruments for measuring the medullary canal of the long bone. Each of the instruments includes an elongated central portion defining opposed first and second ends, a second contact portion extending from the first end of the elongated central portion, the contact portions having a plurality of contact areas for contact with the medullary canal in defining a plurality of relief areas providing clearance between the instrument and the medullary canal.

The method 800 further includes a fourth step 808 of inserting one of the plurality of instruments into the canal. The method 800 further includes a fifth step 810 of providing a plurality of centralizers for implanting into the medullary canal of a long bone. Each of the plurality of centralizers corresponds to one of the plurality of instruments. The method 800 further includes a sixth step 812 of determining the appropriateness of one of the plurality of the instruments and a seventh step 814 of inserting one of the plurality of centralizers corresponding to the one of the plurality of instruments in the canal. The method further includes an eighth step 816 of providing a stem and a ninth step 818 of implanting the stem in the medullary canal of the long bone.

Although the present invention and its advantages have been described in detail, it should be understood that various changes, substitutions, and alterations can be made therein without departing from the spirit and scope of the present invention as defined by the appended claims.

We claim:

1. A method for performing joint arthroplasty comprising:
resecting a long bone;
preparing the medullary canal of a long bone; utilizing at least one of a plurality of instruments for measuring the medullary canal of the long bone, each of said instruments including an elongated central portion defining opposed first and second ends, and an arcuate contact portion extending from the first end of the elongated central portion, the contact portion having a plurality of contact areas each of the plurality of contact areas including an outer periphery, having a circumference, for contact with the medullary canal and defining a plurality of relief areas for providing clearance between the instrument and the medullary canal, wherein the relief area is recessed from the outer periphery of the contact area, such that the relief area interrupts the outer periphery of the contact area, and the relief area does not extend around the entire circumference of the outer periphery;
inserting one of said plurality of instruments into the canal;
determining the appropriateness of said one of said plurality of instruments;
utilizing at least one of a plurality of centralizers for being implanted into the medullary canal of the long bone, each of said plurality of centralizers corresponding to one of said plurality of instruments;
inserting said one of said plurality of centralizers corresponding to said one of said plurality of instruments into the canal;
providing a stem; and
implanting said stem in the medullary canal of a long bone.

2. The method of claim 1, wherein said elongated central portion is generally cylindrical.

3. The method of claim 1, wherein the contact portion is generally pear shaped.

4. The method of claim 1, wherein the elongated central portion includes a plurality of spaced apart marks corresponding to either a metric dimension or an inch dimension.

5. The method of claim 1, wherein the plurality of contact portions is 2 to 6 contact areas for contact with the medullary canal and 2 to 6 relief areas.

6. The method of claim 5, wherein the plurality of contact portions is 4 equally spaced apart contact areas for contact with the medullary canal and 4 equally spaced apart relief areas.

* * * * *